United States Patent [19]

Mahieu et al.

[11] 4,289,752
[45] Sep. 15, 1981

[54] COSMETIC COMPOSITIONS CONTAINING N-ALKYLACRYLAMIDE OR N-ALKYLMETHACRYLAMIDE BASED COPOLYMERS

[75] Inventors: Claude Mahieu, Paris; Christos Papantoniou, Epinay-sur-Seine, both of France

[73] Assignee: Societe Anonyme dite: L'Oreal, Paris, France

[21] Appl. No.: 959,623

[22] Filed: Nov. 13, 1978

Related U.S. Application Data

[62] Division of Ser. No. 783,632, Apr. 1, 1977, abandoned.

[30] Foreign Application Priority Data

Apr. 6, 1976 [LU] Luxembourg .................... 74707
Jul. 12, 1976 [LU] Luxembourg .................... 75371

[51] Int. Cl.$^3$ ................ A61K 7/11; A61K 7/043; A61K 31/78
[52] U.S. Cl. .................................... 424/47; 8/405; 132/7; 424/61; 424/70; 424/81; 526/304
[58] Field of Search .................... 424/81, 61, 47

[56] References Cited

U.S. PATENT DOCUMENTS

| | | | |
|---|---|---|---|
| 2,680,110 | 6/1954 | Loughran et al. | 526/304 |
| 3,025,219 | 3/1962 | Maeder | 526/304 |
| 3,037,963 | 6/1962 | Christenson | 526/304 |
| 3,257,281 | 6/1966 | Maeder | 424/DIG. 1 |
| 3,421,893 | 1/1969 | Taylor | 526/304 |
| 3,459,698 | 8/1969 | Mantell et al. | 526/304 |
| 3,577,517 | 5/1971 | Kubot et al. | 424/81 |
| 3,821,175 | 6/1974 | Daniels et al. | 526/304 |
| 3,925,287 | 12/1975 | Andersen | 526/304 |
| 3,925,293 | 12/1975 | Knechtges et al. | 526/304 |
| 3,975,496 | 8/1976 | Imalley et al. | 526/304 |
| 3,980,769 | 9/1976 | Ghilardi et al. | 424/81 |
| 3,986,825 | 10/1976 | Sokol | 424/81 |
| 3,990,459 | 11/1976 | Papantoniou | 424/81 |
| 4,032,628 | 6/1977 | Papantoniou | 424/81 |
| 4,128,634 | 12/1978 | Hase et al. | 424/81 |
| 4,128,635 | 12/1978 | Hase et al. | 424/81 |
| 4,145,320 | 3/1979 | Ferruti et al. | 424/81 |
| 4,150,110 | 4/1979 | Yoshida et al. | 424/81 X |

*Primary Examiner*—Dale R. Ore
*Attorney, Agent, or Firm*—Cushman, Darby & Cushman

[57] ABSTRACT

The present invention has for its object novel copolymers with a base of N-alkyl acrylamide or methacrylamide and their uses in cosmetics particularly in setting lotions and lacquer and in other preparations such as, for example, nail polish.

11 Claims, No Drawings

COSMETIC COMPOSITIONS CONTAINING N-ALKYLACRYLAMIDE OR N-ALKYLMETHACRYLAMIDE BASED COPOLYMERS

This is a division, of application Ser. No. 783,632 filed Apr. 1, 1977 abandoned.

The present invention has for its object novel copolymers with a base of N-alkyl acrylamide or methacrylamide and their uses in cosmetics particularly in setting lotions and lacquer and in other preparations such as, for example, nail polish.

The present invention also has for its object the process of preparing these novel copolymers.

A great number of synthetic polymers have already been proposed to be used in setting lotions and lacquers and in various types of cosmetic compositions.

It has been found that it was also possible to achieve excellent setting lotions and lacquers and other types of cosmetic compositions with a new class of copolymers.

In contrast with those previously used, these polymers according to the invention make it possible to give the setting lotions or lacquers excellent properties and particularly a good holding of the hairdo.

When these polymers are used in nail polish bases, they make it possible to give a greater resistance, an increased brilliance and a good adherence.

The present invention therefore has for its object novel copolymers comprising groups resulting from copolymerization:

(a) of at least a monomer insoluble in water of the formula:

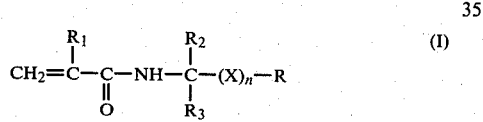

wherein:
R represents a linear or branched alkyl radical having from 1 to 10 carbon atoms,
$R_1$, $R_2$ and $R_3$ represent either a hydrogen atom or a methyl radical, and n is 0 or 1; when n=1 X represents an oxygen atom, and (b) of at least a water soluble monomer of the formula:

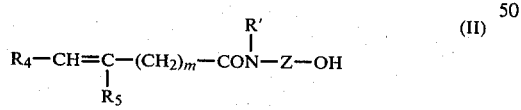

wherein:
R' represents a hydrogen atom or a methyl radical,
Z represents a linear or branched alkylene radical of 1 to 6 carbon atoms, substituted or not by one or two hydroxymethyl functions, and
m is 0 or 1
if m=0,
$R_4$ is either a hydrogen atom or the radical—$COR_6$
$R_6$ being—OH or the radical—NH-$R_7$, $R_7$ being a hydrogen atom or the radical—Z—OH, and
$R_5$ is a hydrogen atom or the radical—$CH_3$,
if m=1,
$R_4$ is a hydrogen atom and $R_5$ is the radical—$COR_6$, $R_6$ having the same signification as above.

In formula (I) above the radical n is preferably equal to zero and $R_1$, $R_2$ and $R_3$ preferably represent methyl radicals, and in formula (II) above the radical Z is preferably taken from the group made up of: —$CH_2$—, —$(CH_2)_2$—, —CH($CH_2H_5$)—$CH_2$—, —C($CH_3)_2$—$CH_2$—, —C($CH_2OH)_2$—$CH_2$—, —C($CH_3)_2$—$CH_2$—CH($CH_3$)—, and —C($CH_3$)($CH_2OH$)—$CH_2$—.

As can be seen from the above definition, the copolymers according to the present invention must necessarily be made up, on the one hand, of at least a monomer insoluble in water and, on the other hand, of at least a monomer soluble in water.

By monomers insoluble in water are meant monomers whose solubility is less than 0.8 g in 100 ml of water at 30° C.

According to a first preferred embodiment of the invention, the copolymers according to the invention are bipolymers that result from the copolymerization of a monomer of the formula (I) and a monomer of formula (II).

According to a second preferred embodiment the copolymers according to the invention are terpolymers or higher copolymers that result from the copolymerization of at least another monomer.

This other monomer which is copolymerized with a monomer of formula (I) and a monomer of formula (II) can be, for example, styrene, N-vinyl pyrrolidone, maleic anhydride or a monomer corresponding to one of formulas (III) to (VII) as follows:

wherein:
Y represents either the radical—CN or the radical—COOH and $R_8$ represents a hydrogen atom or a methyl radical.

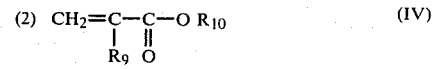

wherein:
$R_9$ represents a hydrogen atom or a methyl radical and $R_{10}$ represents a linear or branched alkyl radical having from 1 to 18 carbon atoms, a radical —$(CH_2)_2N(CH_3)_2$ quaternized or not, a radical —$CH_2$—$CH_2$—$CH_2OH$, a radical

—$CH_2$—CH—$CH_2OH$
|
OH or a radical —$(CH_2$—$CH_2$—$O)_1$—R‴ wherein R‴ represents a methyl or ethyl radical and l is 12,

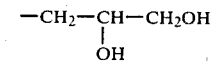

wherein:
$R_{11}$ represents a linear or branched alkyl radical having 1 to 16 carbon atoms, or a phenyl radical, (4) 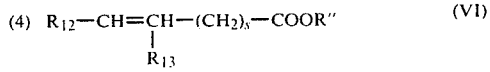 (VI)

wherein:
R'' is an alkyl radical having from 1 to 3 carbon atoms, and s is 0 or 1.
if s=0,
$R_{12}$ represents the radical —COOR'', and
$R_{13}$ represents a hydrogen atom, and
if s=1,
$R_{12}$ represents a hydrogen atom, and
$R_{13}$ represents the radical —COOR'', (5)  (VII)

wherein:
$R_{14}$ represents a saturated linear or branched alkyl radical having 1 to 17 carbon atoms.

According to a third preferred embodiment, the copolymers can be also ter-, tetra-, penta-polymers or higher copolymers that result from copolymerization of more than one monomer of formula (I) and a monomer of formula (II) or a monomer of formula (I) and more than one monomer of formula (II), these monomers optionally being able to be copolymerized in the presence of styrene, N-vinylpyrrolidone, maleic anhydride or another monomer such as those of formula (III) to (VII) above.

The polymers according to the invention can be represented by the following general formula:

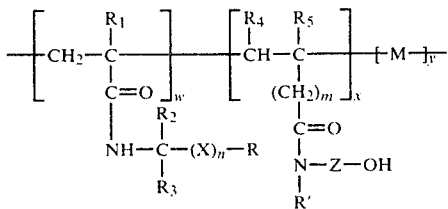

wherein:
the radicals R, R', $R_1$, $R_2$, $R_3$, $R_4$ and $R_5$, n, m, X and Z have the significations given above for formulas (I) and (II), w corresponds to 5 to 95% by weight, x corresponding to 5 to 95% by weight and y corresponds to 0 to 50% by weight, and M represents a styrene, N-vinylpyrrolidone, maleic anhydride group or an unsaturated monomer group such as those of formulas (III) to (VII) given above.

Of the monomers of formula (I) there can be cited in particular: N-tertiobutyl acrylamide, N-octyl acrylamide, N-decyl acrylamide, N-dodecyl acrylamide, N-[(1,1-dimethyl) 1-propyl] acrylamide, N-[(1,1-dimethyl) 1-butyl] acrylamide, N-[(1,1-dimethyl) 1-pentyl] acrylamide, N-isobutyoxy-methylacrylamide and the corresponding methacrylamides.

Of the monomers of formula (II) there can be cited in particular: N-hydroxymethyl acrylamide, N-hydroxymethyl methacrylamide, N-[(2-hydroxy)ethyl] acrylamide, N-[(2-hydroxy) ethyl] methacrylamide, N-hydroxymethyl maleamic acid, N-hydroxymethyl maleamide, N,N'-dihydroxymethyl maleamide, N-hydroxymethyl itaconamic acid, N-hydroxymethyl itaconamide, N,N-dihydroxymethyl itaconamide, N-[(1-hydroxymethyl) propyl] acrylamide, N-[(1-hydroxymethyl) propyl] methacrylamide, N-[1-methyl 1-hydroxymethyl) 1-ethyl] acrylamide, N-[(1-methyl 1-hydroxymethyl) 1-ethyl] methacrylamide, N-[tris 1,1,1-(hydroxymethyl) methyl] acrylamide, N-[tris 1,1,1-(hydroxymethyl)methyl] methacrylamide, N-[(3-hydroxy 1,1-dimethyl) butyl] acrylamide, N-[(3-hydroxy 1,1-dimethyl) butyl] methacrylamide, N-[(2-hydroxy) ethyl] N-methyl acrylamide, N-[(2-hydroxy) ethyl] N-methyl methacrylamide, N-[bis 1,1-(hydroxymethyl) ethyl] acrylamide, and N-[bis 1,1-(hydroxymethyl) ethyl] methacrylamide.

Of the monomers of formula (III) there can be cited in particular: acrylonitrile, methacrylonitrile, acrylic acid and methacrylic acid.

Of the monomers of formula (IV) there can be cited in particular: methyl, ethyl, propyl, isopropyl, butyl, tertio-butyl, hexyl, decyl, dodecyl, octadecyl, 2-hydroxyethyl, N,N dimethyl 2-amino ethyl acrylates and methacrylates, quaternized or not, and ω-methyl or ethyl polyethylene glycol acrylates and methacrylates.

Of the monomers of formula (V) there can be cited in particular: vinyl acetate, vinyl propionate, vinyl butyrate, vinyl laurate, vinyl stearate, vinyl pivalate, vinyl neopeptanoate, vinyl neooctanoate, vinyl neodecanoate, vinyl 2,2,4,4-tetramethyl valerate [,] vinyl 2-isopropyl 2,3-dimethyl butyrate and vinyl benzoate.

Of the monomers of formula (VI) there can be cited in particular: dimethyl maleate, diethyl maleate, dimethyl itaconate and diethyl itaconate.

Of the monomers of formula (VII) there can be cited methyl vinyl ether, ethyl vinyl ether, butyl vinyl ether, isopropyl vinyl ether, octyl vinyl ether, dodecyl vinyl ether and octadecyl vinyl ether.

The copolymers according to the invention preferably have a molecular weight between 1000 and 500,000 and more particularly a molecular weight between 2,000 and 200,000.

In a particular embodiment, the copolymers according to the invention are reticulated with a reticulation agent in a proportion between 0.01 and 2% by weight in relation to the total weight of the monomers used to react.

Of the various reticulation agents that can be used, there can be cited in particular; diethylene glycol dimethacrylate, diallyl ether, tetra allyloxyethane, ethylene glycol dimethacrylate and ethylene glycol diacrylate.

According to a particular embodiment when the radical $R_4$ represents a free carboxylic acid function, the latter can be neutralized with at least an organic base such as monoethanolamine, diethanolamine, triethanolamine, isopropanolamines such as triisopropanolamine, morpholine and certain amino alcohols such as 2-amino, 2-methyl propanol and 2-amino 2-methyl 1,3-propanediol.

The carboxylic functions can be neutralized with these organic bases in a proportion between 10 and 150%.

The present invention also has for its object a process of preparing copolymers as described above.

These copolymers can be prepared by copolymerization in solution in an organic solvent such as alcohols, esters, ketones or hydrocarbons.

Of these solvents there can be cited in particular: methanol, isopropanol, ethanol, ethyl acetate, ethyl methyl ketone, benzene, etc.

Copolymerization can also take place in suspension or in emulsion in an inert solvent such as water.

The copolymerization can also take place en masse.

These polymerizations can be performed in the presence of a polymerization catalyst generating free radicals, such as benzoyl peroxide, lauroyl peroxide, azo-bis-isobutyronitrile, hydrogen peroxide, various oxydoreduction couples such as: $(NH_4)_4 S_2O_8$, $FeCl_2$, etc.

The catalyst concentration varies between 0.2 and 10% by weight in relation to the monomers caused to react and as a function of the molecular weight of the copolymers it is desired to obtain.

The present invention further has for its object the use of the novel copolymers described above in cosmetic compositions.

The present invention in particular has for its object cosmetic compositions in the form of lacquers packaged or not in aerosol form, hair setting lotions, compositions for treating hair, dye supports, shampoos or again in the form of rinses.

By rinses are understood compositions that are applied after washing the hair.

The copolymer concentration in these various type of compositions is generally between 0.2 and 30% by weight in relation to the total weight of the compositions.

The aerosol lacquers according to the invention can be made by packaging in an aerosol bomb from 0.2 to 8% by weight of a copolymer according to the invention, from 6 to 30% and preferably from 8 to 25% by weight of an alcohol, the remainder essentially made up of a liquified propellent gas under pressure such as dichlorodifluoromethane, trichlorofluoromethane, nitrous oxide or carbon dioxide gas or mixtures thereof.

The alcohol used is preferably ethyl alcohol or isopropyl alcohol.

The setting lotion according to the invention can be, for example, made by introduction in a water-alcohol solution having a strength of 20 to 66% alcohol of 0.3 to 6% by weight of a copolymer according to the invention.

According to another embodiment, the polymers, and particularly those comprising methylol functions, can be introduced into the compositions in the form of aqueous or water-alcohol solutions and can be applied to weakened or degraded hair to obtain a reinforcement and better holding of the hair setting.

In this case, the compositions are preferably applied simultaneously with an acid catalyst.

Of the acid catalysts that can be used there can be cited in particular: hydrochloric acid, lactic acid, and other inorganic or organic acids.

The copolymers according to the invention can also be used for making nail polish and in this case they make it possible to replace advantageously Santolite and in certain cases also nitrocellulose.

In this particular embodiment, the copolymers are present in a proportion between 2 and 30% in relation to the total weight of the composition.

The various compositions as described above can also contain other cosmetic adjuvants such as, for example, perfumes, dyes, preservatives, plasticizers, cationic products, non-ionic products, silicones and other cosmetic resins.

To give a better understanding of the invention there will now be described by way of non-limiting illustration various examples of preparation of the copolymers and various examples of their base compositions.

EXAMPLES OF PREPARATION OF COPOLYMERS

Example 1

Into a 1-liter flask provided with a mechanical stirrer, a nitrogen intake tube, a thermometer and a condenser are introduced 200 g of ethanol, 35 g of N-tertiobutyl acrylamide, 42.5 g of N-hydroxymethylacrylamide and 22.5 g of methyl methacrylate. Then 1 g of azo-bis-isobutyronitrile is introduced into the reaction mixture. The reaction mixture is heated at 80° C. for 8 hours with an apparatus equipped with a thermostat. It is then allowed to cool to ambient temperature.

The solution in then poured, drop by drop, into a receptacle containing ethyl acetate as the precipitant. The precipitated polymer is then filtered and dried under reduced pressure.

Yield: 97%.

Viscosity: 2.90 cpo [in 5% solution in dimethylformamide (DMF) at 34.6° C.].

Example 2

According to the process described in example 1 there are polymerized:

| | |
|---|---|
| N-tertiobutylacrylamide | 50 g |
| N-hydroxymethylacrylamide | 40 g |
| Vinyl acetate | 10 g |
| Azo-bis-isobutyronitrile | 1 g |

Yield: 79%.

Viscosity: 2.34 cpo [in 5% solution in DMF at 34.6° C.]

Example 3

According to the process described in example 1 there are polymerized:

| | |
|---|---|
| N-tertiobutylacrylamide | 40 g |
| N-hydroxymethylacrylamide | 40 g |
| Diethyl maleate | 20 g |
| Azo-bis-isobutyronitrile | 1 g |

Yield: 67%.

Viscosity: 2.38 cpo (in 5% solution in DMF at 34.6° C.).

Example 4

According to the process described in example 1 there are polymerized:

| | |
|---|---|
| N-tertiobutylacrylamide | 40 g |
| N-hydroxymethylacrylamide | 50 g |
| Butyl methacrylate | 10 g |
| Azo-bis-isobutyronitrile | 1 g |

Yield: 80%.

Viscosity: 2.80 cpo (in 5% solution in DMF at 34.6° C.).

Example 5

According to the process described in example 1 there are copolymerized:

| | |
|---|---|
| N-tertiobutylacrylamide | 90 g |

| | |
|---|---|
| N-hydroxymethylacrylamide | 10 g |
| Azo-bis-isobutyronitrile | 1 g |

The reaction solution is then poured, drop by drop, into a container containing hexane. The precipitated polymer is then filtered and dried under reduced pressure.
Yield: 80%.
Viscosity: 10.0 cpo (in 5% solution in DMF at 34.6° C.).

Example 6

According to the process of example 1 there are co-polymerized:

| | |
|---|---|
| N-tertiobutylacrylamide | 50 g |
| N-hydroxylmethylacrylamide | 40 g |
| Acrylonitrile | 10 g |
| Azo-bis-isobutyronitrile | 1 g |

Yield: 73%
Viscosity: 1.95 cpo (in 5% solution in DMF at 34.6° C.)

Example 7

According to the process of example 1 there are co-polymerized:

| | |
|---|---|
| N-tertiobutylacrylamide | 40 g |
| N-[tris 1.1.1-(hydroxymethyl) methyl] acrylamide | 40 g |
| Lauryl methacrylate | 20 g |
| Azo-bis-isobutyronitrile | 1 g |

Yield: 67%
Viscosity: 2.00 cpo (in 5% solution in DMF at 34.6° C.).
In this example the precipitating agent according to example 1 is replaced with acetone.

Example 8

According to the process described in example 1 above there are polymerized:

| | |
|---|---|
| N-tertiobutylacrylamide | 50 g |
| N-hydroxymethylacrylamide | 30 g |
| Butyl vinyl ether | 20 g |
| Azo-bis-isobutyronitrile | 1 g |

The reaction solution is then poured drop by drop into a container containing acetone. The precipitated polymer is then filtered and dried under reduced pressure.
Yield: 32.5%
Viscosity: 3.67 cpo (in 5% solution in DMF at 34.6° C.).

Example 9

According to the process of example 1 there are co-polymerized:

| | |
|---|---|
| N-tertiobutylacrylamide | 50 g |
| N-hydroxymethylacrylamide | 40 g |
| Methyl acrylate | 10 g |
| Azo-bis-isobutyronitrile | 1 g |

As in the preceding example the reaction solution is then poured drop by drop into a container containing acetone. The precipitated polymer is then filtered and dried under reduced pressure.
Yield: 67.5%.
Viscosity: 3.03 cpo (in 5% solution in DMF at 34.6° C.).

Example 10

According to the process described in example 1 there are polymerized:

| | |
|---|---|
| N-tertiobutylacrylamide | 50 g |
| N-hydroxymethylacrylamide | 40 g |
| Styrene | 10 g |
| Azo-bis-isobutyronitrile | 1 g |

Yield: 84.5%
Viscosity: 2.23 cpo (in 5% solution in DMF at 34.6° C.).

Example 11

According to the process of example 1 there are co-polymerized:

| | |
|---|---|
| N-tertiobutylacrylamide | 50 g |
| N-hydroxymethylacrylamide | 40 g |
| Diethyl maleate | 10 g |
| Azo-bis-isobutyronitrile | 1 g |

Yield: 91%
Viscosity: 2.56 cpo (in 5% solution in DMF at 34.6° C.).

Example 12

According to the process of example 1 there are co-polymerized:

| | |
|---|---|
| N-tertiobutylacrylamide | 50 g |
| N-hydroxymethylacrylamide | 40 g |
| Vinyl benzoate | 10 g |
| Azo-bis-isobutyronitrile | 1 g |

Yield: 76%
Viscosity: 2.89 cpo (in 5% solution in DMF at 34.6° C.).

Example 13

According to the process of example 1 there are co-polymerized:

| | |
|---|---|
| N-tertiobutylacrylamide | 30 g |
| N-[(1-methyl 1-hydroxymethyl) 1-ethyl] acrylamide | 50 g |
| Methyl methacrylate | 20 g |
| Azo-bis-isobutyronitrile | 1 g |

The reaction solution is then poured drop by drop into a container containing petroleum ether. The precipitated polymer is then filtered and dried under reduced pressure.
Yield: 94%

Viscosity: 2.34 cpo (in 5% solution in DMF at 34.6° C.).

Example 14

According to the process described in example 1 there are copolymerized:

| | |
|---|---|
| N-tertiobutylacrylamide | 30 g |
| N-[(1-methyl 1-hydroxymethyl) ethyl] acrylamide | 20 g |
| 2-hydroxyethyl methacrylate | 30 g |
| Methyl methacrylate | 20 g |
| Azo-bis-isobutyronitrile | 1 g |

The reaction solution is then poured drop by drop into a container containing petroleum ether. The precipitated polymer is then filtered and dried under reduced pressure.

Yield: 89%

Viscosity: 2.68 cpo (in 5% solution in DMF at 34.6° C.).

Example 15

According to the process described in example 1 there are polymerized:

| | |
|---|---|
| N-tertiobutylacrylamide | 50 g |
| N-[(1-methyl 1-hydroxymethyl) 1-ethyl] acrylamide | 40 g |
| Acrylic acid | 10 g |
| Azo-bis-isobutyronitrile | 1 g |

Viscosity: 2.39 cpo (in 5% solution in DMF at 34.6° C.

Acid value: 55.8

Example 16

According to the process described in example 1 there are polymerized:

| | |
|---|---|
| N-tertiobutylacrylamide | 45 g |
| N-hydroxymethylacrylamide | 20 g |
| Acrylic acid | 5 g |
| N-vinylpyrrolidone | 30 g |
| Azo-bis-isobutyronitrile | 1 g |

Viscosity: 2.52 cpo
Acid value: 27

Example 17

According to the process described in example 1 there are polymerized:

| | |
|---|---|
| N-tertiobutylacrylamide | 50 g |
| N-[(1-methyl 1-hydroxymethyl) 1-ethyl] acrylamide | 40 g |
| Methacrylic acid | 10 g |
| Azo-bis-isobutyronitrile | 1 g |
| Acid value: 71.3 | |

Other examples of copolymers (examples 18 to 28) are given in Table I. All these copolymers have been prepared according to example 1 except example 24 in which 0.5 g of catalyst and 50 g of ethanol were used.

TABLE I

| EXAMPLES | 18 | 19 | 20 | 21 | 22 | 23 | 24 | 25 | 26 | 27 | 28 |
|---|---|---|---|---|---|---|---|---|---|---|---|
| N-T-BUTYL ACRYLAMIDE | 30 | 50 | 20 | 60 | 85 | 40 | 40 | 50 | 40 | 30 | 55 |
| N-HYDROXY METHYL ACRYLAMIDE | | 40 | | | | | | | | | 45 |
| N-[(1-METHYL 1-HYDROXY-METHYL) 1-ETHYL] ACRYLAMIDE | 30 | | 25 | | 5 | 45 | 5 | 5 | | 15 | |
| N-[TRIS 1,1,1-(HYDROXYMETHYL) METHYL] ACRYLAMIDE | | | | 30 | | | | 40 | | | |
| N-VINYL PYRROLIDONE | 40 | | | | | | | | | | |
| 2-HYDROXY ETHYL METHACRYLATE | | | 55 | | | | | | | 35 | |
| METHACRYLONITRILE | | 10 | | | | | | | | | |
| METHYL METHACRYLATE | | | | | | | 10 | | | 20 | |
| DIMETHYL AMINO ETHYL METHACRYLATE | | | | | | | 35 | 35 | | | |
| ACRYLIC ACID | | | | 10 | | | | | | | |
| METHACRYLIC ACID | | | | | 10 | | 10 | 10 | | | |
| POLYETHYLENE GLYCOL MONO-METHYL ETHER METHACRYLATE | | | | | | 15 | | | 20 | | |
| PRECIPITANT | ① | ① | ① | ③ | ③ | ① | ④ | ④ | ③ | ① | ② |
| VISCOSITY cpo 5% DMF 34.6° C. | 2.33 | 1.95 | 2.24 | 2.54 | 2.07 | 1.51 | 5.97 | 2.50 | 2.73 | 1.93 | 3.16 |
| ACID VALUE | | | | 7.77 | 5.95 | | 64.8 | 66.5 | | | |

Ref:
① ethyl acetate
② acetone
③ petroleum ether
④ diethyl ether

EXAMPLES OF COSMETIC COMPOSITIONS

Example A

There is prepared according to the invention a setting lotion by mixing the following ingredients:

| | |
|---|---|
| Polymer prepared according to example 1 | 2 g |
| Perfume | 0.1 g |
| Ethyl alcohol | 45 g |
| Water sufficient for | 100 g |

This setting lotion, applied in a conventional way, makes it possible to give the hair a brilliant appearance and an excellent holding in time.

In this example, the copolymer according to example 1 can be advantageously replaced by the same amount of one of the polymers prepared according to examples 10 and 13.

Example B

There is prepared according to the invention a setting lotion by mixing the following ingredients:

| | |
|---|---|
| Polymer prepared according to example 3 | 3.5 g |
| Perfume | 0.1 g |
| Dye sufficient to dye the lotion | 0.2 g |
| Isopropyl alcohol | 40 g |
| Water sufficient for | 100 g |

After impregnation of the hair with the above lotion, the hair is put up in rollers having a diameter of 15 to 30 mm and the hair is dried by external bringing in of heat. After removal of the rollers, an excellent setting having a good hold in time is obtained.

In the example the polymer according to example 3 can advantageously be replaced by the same amount of the polymer prepared according to example 7.

Example C

There is prepared according to the invention a setting lotion by mixing the following ingredients:

| | |
|---|---|
| Polymer prepared according to example 4 | 2 g |
| Perfume | 0.1 g |
| Ethyl alcohol | 45 g |
| Water sufficient for | 100 g |

In this example the polymer prepared according to example 4 can be replaced by the same amount of the polymer prepared according to example 28.

Example D

There is prepared according to the invention a hair lacquer by mixing the following ingredients:

| | |
|---|---|
| Polymer obtained according to example 2 | 6.5 g |
| Perfume | 0.2 g |
| Ethanol | 100 g |

25 g of this solution are packaged in an aerosol bomb with 45 g of trichlorofluoromethane and 30 g of dichlorodifluoromethane.

By spraying of this mixture on hair there is obtained a good fixing, the hair being brilliant and soft to the touch.

By light brushing, the resin is very easily eliminated.

In this example, the polymer according to example 2 can advantageously be replaced by the same amount of one of the polymers prepared according to examples 8 to 14.

Example E

A hair lacquer is prepared by mixing the following ingredients:

| | |
|---|---|
| Polymer obtained according to example 6 | 8 g |
| Ethyl alcohol sufficient for | 100 g | trichlorofluoromethane and 30 g of dichlorofluoromethane.

After spraying of this lacquer on the hair, the latter is brilliant and not sticky. This lacquer is eliminated perfectly by brushing and there is no accumulation of resin on the hair even after several applications.

In this example, the polymer according to example 6 can be replaced by the same amount of polymer prepared according to examples 12 and 18 to 20.

Example F

There is prepared according to the invention a composition for treating hair by mixing the following ingredients:

| | |
|---|---|
| Polymer prepared according to example 4 | 1 g |
| Perfume | 0.1 g |
| Water sufficient for | 100 g |

This composition is applied for several minutes to hair that has previously been shampooed and rinsed with water.

After another rinsing with water brilliant and silky hair is obtained which combs out very easily during dressing.

In this example the polymer according to example 4 can be replaced by the same amount of the polymer prepared according to example 11 or example 23.

Example G

A setting lotion is prepared according to the invention by mixing the following ingredients:

| | |
|---|---|
| Polymer prepared according to example 15 (quaternized with dimethyl sulfate) | 2 g |
| 2-amino 2-methyl 1-propanol sufficient for neutralization | |
| Perfume | 0.1 g |
| Ethyl alcohol | 45 g |
| Water sufficient for | 100 g |

This setting lotion, applied in a conventional way, makes it possible to give the hair a brilliant appearance and an excellent holding in time.

In this example the polymer according to example 15 can be replaced by the same amount of the polymer prepared according to example 25 or 24 also quaternized with dimethyl sulfate.

Example H

A setting lotion is prepared according to the invention by mixing the following ingredients:

| | |
|---|---|
| Polymer prepared according to example 16 | 3.5 g |
| 2-amino 2-methyl 1-propanol sufficient for neutralization | |
| Perfume | 0.1 g |
| Dye sufficient to dye the lotion | 0.2 g |
| Isopropyl alcohol | 40 g |
| Water sufficient for | 100 g |

After impregnation of the hair with the above lotion, the hair is put up in rollers having a diameter of 15 to 30 mm and the hair is dried by external supply of heat. After removal of the rollers, an excellent setting having a good holding in time is obtained.

In this example the polymer prepared according to example 16 can be replaced by the same amount of one of the polymers prepared according to examples 15, 22 and 26.

Example I

There is prepared according to the invention a setting lotion by mixing the following ingredients:

| Polymer prepared according to example 17 | 2 g |
|---|---|
| 2-amino 2-methyl 1,3-propanediol sufficient for neutralization | |
| Perfume | 0.1 g |
| Ethyl alcohol | 45 g |
| Water sufficient for | 100 g |

Example I

A hair lacquer is prepared according to the invention by mixing the following ingredients:

| Polymer obtained according to example 27 | 6.5 g |
|---|---|
| Diethanolamine sufficient for neutralization | |
| Perfume | 0.2 g |
| Ethanol sufficient for | 100 g |

25 g of this solution are packaged in an aerosol bomb with 45 g of trichlorofluoromethane and 30 g of dichlorodifluoromethane.

By spraying of this mixture on hair a good fixing is obtained, the hair being brilliant and soft to the touch.

By light brushing, the resin is easily eliminated.

In this example, the polymer according to example 27 can be replaced by the same amount of the polymer prepared according to example 28.

Example K

An aerosol lacquer is prepared according to the invention by mixing the following ingredients:

| Polymer obtained according to example 22 | 5 g |
|---|---|
| 2-amino 2-methyl 1,3-propanediol sufficient for neutralization | |
| Perfume | 0.07 g |
| Ethanol sufficient for | 100 g |

93 g of this solution are then packaged in an aerosol bomb and carbon dioxide is introduced to bring the internal pressure to about 8 bars.

Example L

A nail polish is prepared according to the invention by mixing the following ingredients:

| Nitrocellulose | 12 g |
|---|---|
| Copolymer according to example 5 | 6 g |
| Camphor | 2 g |
| Butyl phthalate | 5 g |
| Ethyl alcohol | 4 g |
| Butyl alcohol | 4 g |
| Toluene | 20 g |
| Ethyl acetate | 15 g |
| Butyl acetate | 32 g |
| | 100 g |

This base varnish can be used to obtain a polish for coloring the nails by adding thereto certain dyes and an antisediment mixture.

Antisediment mixture:

| Bentone | 1.20 g |
|---|---|
| Phosphoric acid | 0.02 g |
| Dyes: | |
| Titanium oxide | 1 g |
| D and C Red 7 | 0.4 g |
| D and C red 11 | 0.3 g |

| D and C red 5 | 0.2 g |
|---|---|
| D and C yellow 5 | 0.6 g |

In this example the polymer according to example 5 can be replaced by one of the polymers prepared according to examples 4, 7, 9 and 29.

Example M

A nail polish is prepared according to the invention which has the following composition:

| Copolymer according to example 29 | 20 g |
|---|---|
| Toluene | 20 g |
| Butyl phthalate | 3 g |
| Camphor | 2 g |
| Ethyl acetate | 20 g |
| Butyl acetate | 35 g |
| | 100 g |

This base varnish can be used for preparing a polish for coloring the nails, in this case, the latter is mixed with the following ingredients:

Antisediment agent:

| Bentone 27 | 0.6 g |
|---|---|
| Bentone 38 | 0.6 g |
| Phosphoric acid | 0.01 g |
| Dyes: | |
| Guanine | 1 g |
| D and C red 7 | 0.2 g |
| D and C red 11 | 0.1 g |

In this example the polymer prepared according to example 23 can be replaced by the same amount of one of the polymers prepared according to examples 13 and 14.

We claim:

1. A hair setting lotion comprising in a hydroalcoholic solution a copolymer which is the polymerization of:

(a) a water-insoluble monomer of the formula

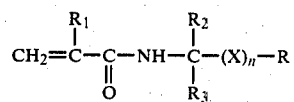

wherein:

R represents alkyl having 1–10 carbon atoms, $R_1$, $R_2$ and $R_3$ each independently represent hydrogen or methyl, n=0 or 1 and when n=1, X represents oxygen, and (b) a water soluble monomer of the formula

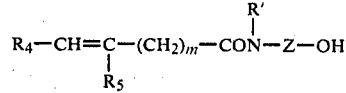

wherein

R' represents hydrogen or methyl,

Z represents alkylene having 1–6 carbon atoms or alkylene having 1–6 carbon atoms and substituted by 1–2 hydroxymethyl groups, m is 0 or 1, when m is 0, R$_4$ is hydrogen or —COR$_6$ wherein R$_6$ is OH or —NH—R$_7$, wherein R$_7$ is hydrogen or —Z—OH wherein Z has the meaning given above, and R$_5$ is hydrogen or —CH$_3$, and when m is 1, R$_4$ is hydrogen and R$_5$ is —COR$_6$ wherein R$_6$ has the meaning given above, said copolymer having a molecular weight between 1,000 and 500,000, and being present in an amount between 0.3 and 6 percent by weight of said lotion.

2. The hair setting lotion of claim 1 wherein the water-insoluble monomer is N-tert. butyl acrylamide.

3. The hair setting lotion of claim 1 wherein said hydroalcoholic solution is an aqueous solution of ethanol or isopropanol present in an amount ranging from 20–66 percent by weight of said hydroalcoholic solution.

4. An aerosol hair lacquer composition for setting the hair, packaged under pressure in an aerosol container comprising 6 to 30 percent by weight of an alcohol and 0.2 to 8 percent by weight of a copolymer which is the polymerization of:

(a) a water-soluble monomer of the formula

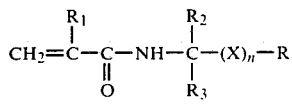

wherein

R represents alkyl having 1–10 carbon atoms,

R$_1$, R$_2$ and R$_3$ each independently represent hydrogen or methyl, n=0 or 1 and when n=1, X represents oxygen, and (b) a water soluble monomer of the formula

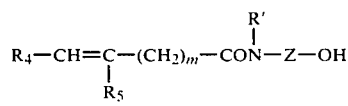

wherein

R' represents hydrogen or methyl,

Z represents alkylene having 1–6 carbon atoms or alkylene having 1–6 carbon atoms and substituted by 1–2 hydroxymethyl groups, m is 0 or 1, when m is 0, R$_4$ is hydrogen or —COR$_6$ wherein R$_6$ is OH or —NH—R$_7$ wherein R$_7$ is hydrogen or —Z—OH wherein Z has the meaning given above, and R$_5$ is hydrogen or —CH$_3$, and when m is 1, R$_4$ is hydrogen and R$_5$ is —COR$_6$ wherein R$_6$ has the meaning given above;

said copolymer having a molecular weight between 1,000 and 500,000, the remainder being essentially a liquified propellant gas.

5. The aerosol cosmetic composition of claim 4 wherein the water-insoluble monomer is N-tert. butyl acrylamide.

6. The aerosol cosmetic composition of claim 4 wherein said alcohol is ethanol or isopropanol.

7. The aerosol composition of claim 4 wherein said alcohol is present in an amount between 8 and 25 percent by weight of said composition.

8. In a nail polish composition the improvement comprising the inclusion therein of 2 to 30 percent by weight based on the total weight of said composition of a copolymer which is the polymerizate of (a) a water-insoluble monomer of the formula

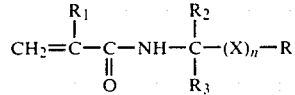

wherein

R represents alkyl having 1–10 carbon atoms,

R$_1$, R$_2$ and R$_3$ each independently represent hydrogen or methyl, n=0 or 1 and when n=1, X represents oxygen, and (b) a water soluble monomer of the formula

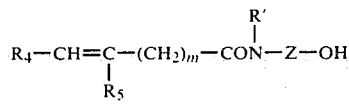

wherein

R' represents hydrogen or methyl,

Z represents alkylene having 1–6 carbon atoms or alkylene having 1–6 carbon atoms and substituted by 1–2 hydroxymethyl groups, m is 0 or 1, when m is 0, R$_4$ is hydrogen or —COR$_6$ wherein R$_6$ is OH or —NH—R$_7$ wherein R$_7$ is hydrogen or —Z—OH wherein Z has the meaning given above, and R$_5$ is hydrogen or —CH$_3$, and when m is 1, R$_4$ is hydrogen and R$_5$ is —COR$_6$ wherein R$_6$ has the meaning given above, said copolymer having a molecular weight between 1,000 and 500,000.

9. The nail polish of claim 8 wherein the water-insoluble monomer is N-tert.butyl acrylamide.

10. A process for setting the hair comprising applying to said hair an effective hair setting amount of the hair setting lotion of claim 1 and setting the hair.

11. A process for setting the hair comprising applying to the hair an effective hair setting amount of the aerosol hair lacquer composition of claim 4.

* * * * *